US005702506A

United States Patent [19]

Shih et al.

[11] Patent Number: 5,702,506

[45] Date of Patent: Dec. 30, 1997

[54] METHOD AND DEVICE FOR AEROSOL SIZE-SELECTIVE SAMPLING

[75] Inventors: Tung-Sheng Shih; Wen-Yu Yeh; Chih-Chieh Chen; Chane-Yu Lai, all of Taipei, Taiwan

[73] Assignee: Institute of Occupational Safety and Health, Council of Labor Affairs, Executive Yuan, Taipei, Taiwan

[21] Appl. No.: 733,081

[22] Filed: Oct. 16, 1996

[51] Int. Cl.$^6$ ..................... B01D 46/12

[52] U.S. Cl. ..................... 95/287; 95/286; 73/31.02; 55/270; 55/343; 55/350.1

[58] Field of Search ..................... 55/270, 315, 343, 55/350.1; 73/31.01, 31.02, 31.03, 864.71; 95/273, 286, 287

[56] References Cited

U.S. PATENT DOCUMENTS

| | | | |
|---|---|---|---|
| 1,493,110 | 5/1924 | Diehl | 55/286 X |
| 3,657,992 | 4/1972 | Minnick, Jr. | 55/315 X |
| 3,953,182 | 4/1976 | Roth | 55/270 |
| 4,155,247 | 5/1979 | Kaczmarek et al. | 55/270 X |
| 4,277,259 | 7/1981 | Rouxrbehler et al. | 55/270 X |
| 4,327,575 | 5/1982 | Locker | 73/31.02 |
| 4,350,507 | 9/1982 | Greenough et al. | 55/270 |
| 4,902,318 | 2/1990 | Stevens et al. | 55/270 |
| 5,294,236 | 3/1994 | Baird | 55/270 |
| 5,498,271 | 3/1996 | Marple et al. | 55/270 X |

*Primary Examiner*—Robert Spitzer

*Attorney, Agent, or Firm*—Bacon & Thomas

[57] ABSTRACT

An aerosol size-selective sampling device is composed of pre-filter, a base housing, and a collector. The device is intended to take an aerosol sample from a given atmospheric air. The pre-filter is composed of two or more porous filtration materials arranged in one end of the base housing in a parallel manner for allowing the atmospheric air to pass therethrough in a parallel and diverting pattern before the atmospheric air is allowed to pass in a converging manner through the collector which is located in another end of the base housing. The pre-filter is able to attain a desired penetration rate profile as a function of an aerodynamic diameter of aerosol contained in the atmospheric air within a predetermined range of aerodynamic diameter.

14 Claims, 14 Drawing Sheets

METHOD AND DEVICE FOR AEROSOL SIZE-SELECTIVE SAMPLING

FIELD OF THE INVENTION

The present invention relates generally to a method and a device for aerosol size-selective sampling, and more particularly to a parallel-type method and a parallel-type device for aerosols size-selective sampling.

BACKGROUND OF THE INVENTION

The method for assessing the aerosol harmful to the respiratory organs of the industrial workers involves the collection of the aerosol by means of the filter paper, and the measurement of the collected aerosols in terms of the weight concentration.

Generally speaking, the areas of such an investigation as described above include the initial area of the respiratory system in the head portion, the bronchial area comprising the bronchia and the ciliate area, and the alveolar area comprising the non-ciliate portion and the lung sac.

Depending on the physical properties of the toxic fine particles, the deposition of such fine particles may take place in certain specific respiratory areas, which are generally immune from the aerosol in view of the relatively large size of such aerosol. For example, the silicon-containing aerosol are seldom able to travel to arrive at the alveolar area of a person to inflict the silicosis on the person in view of the fact that such silicon-containing aerosol have relatively large aerodynamic diameters and an inertia sinking effect.

It is therefore necessary to develop a method for aerosol size-selective sampling, which is specifically designed to attain a meaningful measurement of the aerosol concentration in different parts of the respiratory system. As a result, certain organizations responsible for establishing the standard methods have introduced the ideal size-selective sampling standards on the basis of the aerodynamic diameter serving as a function. The examples of such organizations are described hereinafter.

As far as the respirable fine particles are concerned, British Medical Research Council (BMRC) had made some suggestions, which were adopted in 1959 by Johannesburg Pneumoconiosis Conference.

In 1983, International Standard Organization (ISO) proposed standards for size-selective sampling of the inspirable or inhalable fine particles in the thoracic cavity and the alveolar area.

In 1985, American Conference of Governmental Industrial Hygienists (ACGIH) proposed standards for size-selective sampling of the inspirable fine particles.

In 1987, The United States Environmental Protection Agency (EPA) proposed the PM 10 sampling standards similar in definition to the standards proposed respectively by ISO and ACGIH.

On the basis of the above suggestions regarding the size-selective sampling, the environmental aerosols are redefined and reclassified as the inspirable aerosol, the thoracic aerosol, and the respirable aerosols. However, these criteria proposed by the afore-mentioned organizations have not been regarded as being workable and acceptable. For this reason, it is imperative that new criteria are established such that they are universally recognized, and that they can be implemented economically.

Sidney C. Soderholm proposed three size-selective samplings for the inhalable aerosol, the thoracic aerosol and the respirable aerosol. For more details, please refer to Table 1 and Ann. Occup. Hyg. 33(3):301–320 (1989). These criteria proposed by Soderholm have been recognized and adopted by various international organizations, such as ACGIH, ISOCEN (Commite Europeen de Normalisation). The internationally-defined size-selective sampling curves can be plotted respectively for the inhalable aerosol, the thoracic aerosol and the respirable aerosol on the basis of the data of aerodynamic diameters of the aerosol and the penetration rates of the aerosol. For more details, please refer to Table 1 and FIG. 1. In FIG. 1, the aerodynamic diameters of the aerosol are plotted against the penetration rates of the aerosol so as to obtain the size-selective sampling curves. The dotted line in FIG. 1 is a 50% demarcation line of the penetration rate. It is therefore readily apparent from the coordinate that the 50% cut-off size ($D_{50}$) of the respirable curve is 4 μm. Similarly, the 50% cut-off sizes of the thoracic curve and the inhalable curve are respectively 10 μm and 100 μm.

TABLE 1

| Inhalable | | Thoracic | | Respirable | |
|---|---|---|---|---|---|
| Aerodynamic diameter (mm) | Penetration rate (%) | Aerodynamic diameter (mm) | Penetration rate (%) | Aerodynamic diameter (mm) | Penetration rate (%) |
| 0.50 | 98.52 | 0.50 | 98.52 | 0.50 | 98.52 |
| 1.00 | 97.09 | 1.00 | 97.09 | 1.00 | 97.07 |
| 2.00 | 94.35 | 2.00 | 94.35 | 2.00 | 91.37 |
| 3.00 | 91.76 | 3.00 | 91.73 | 3.00 | 73.86 |
| 4.00 | 89.33 | 4.00 | 88.96 | 4.00 | 49.98 |
| 5.00 | 87.04 | 5.00 | 85.42 | 5.00 | 29.97 |
| 6.00 | 84.88 | 6.00 | 80.55 | 6.00 | 16.77 |
| 7.00 | 82.85 | 7.00 | 74.16 | 7.00 | 9.05 |
| 8.00 | 80.94 | 8.00 | 66.57 | 8.00 | 4.81 |
| 9.00 | 79.14 | 9.00 | 58.33 | 9.00 | 2.54 |
| 10.00 | 77.44 | 10.00 | 50.03 | 10.00 | 1.35 |
| 11.00 | 75.84 | 11.00 | 42.13 | 11.00 | 0.72 |
| 12.00 | 74.34 | 12.00 | 34.94 | 12.00 | 0.39 |
| 13.00 | 72.92 | 13.00 | 28.63 | 13.00 | 0.21 |
| 14.00 | 71.59 | 14.00 | 23.23 | 14.00 | 0.12 |
| 15.00 | 70.33 | 15.00 | 18.70 | 15.00 | 0.07 |
| 16.00 | 69.15 | 16.00 | 14.96 | 16.00 | 0.04 |

TABLE 1-continued

| Inhalable | | Thoracic | | Respirable | |
|---|---|---|---|---|---|
| Aerodynamic diameter (mm) | Penetration rate (%) | Aerodynamic diameter (mm) | Penetration rate (%) | Aerodynamic diameter (mm) | Penetration rate (%) |
| 17.00 | 67.03 | 17.00 | 11.91 | 17.00 | 0.02 |
| 18.00 | 66.98 | 18.00 | 9.45 | 18.00 | 0.01 |
| 19.00 | 65.99 | 19.00 | 7.49 | 19.00 | 0.01 |
| 20.00 | 65.06 | 20.00 | 5.92 | 20.00 | 0.00 |
| 30.00 | 58.27 | 30.00 | 0.57 | | |
| 40.00 | 54.54 | 40.00 | 0.06 | | |
| 50.00 | 52.49 | 50.00 | 0.01 | | |
| 70.00 | 50.75 | | | | |
| 90.00 | 50.23 | | | | |
| 100.00 | 50.12 | | | | |

SUMMARY OF THE INVENTION

It is therefore the primary objective of the present invention to provide a device for the aerosol size-selective sampling. The device has a pre-filter which is able to attain a desired penetration rate profile as a function of an aerodynamic diameter within a predetermined range of aerosol.

It is another objective of the present invention to provide a method for the aerosol size-selective sampling. The method is capable of attaining a sampling result in conformity with a desired penetration rate profile as a function of an aerodynamic diameter within a predetermined range of aerosol.

In keeping with the principle of the present invention, the foregoing objectives of the present invention are attained by a method for the aerosol size-selective sampling, in which an aerosol size-selective sampling device is employed to carry out the aerosol size-selective sampling in a given atmosphere. The aerosol size-selective sampling device comprises a pre-filter, a base housing and a collector. The method of the present invention is characterized in that the pre-filter comprises two or more parallel porous filtration materials and is received in an air inlet end of the base housing. As soon as a pump is started, the atmospheric air is forced into the air inlet end of the base housing such that the atmospheric air is caused to pass through the two or more parallel porous filtration materials of the pre-filter in a parallel and diverting manner. Thereafter, the atmospheric air is caused to pass in a converging manner through the collector located in an air outlet end of the base housing. The pre-filter is able to attain a desired penetration rate profile as a function of an aerodynamic diameter within a predetermined range of aerosol contained in the atmospheric air.

The device used in the method of the present invention comprises a base housing and a pre-filter. The base housing is provided with an air inlet end and an air outlet end which is adapted to accommodate a collector. The pre-filter is disposed in said air inlet end of said base housing.

The device of the present invention is characterized in that its pre-filter comprises two or more porous filtration materials arranged in a parallel manner.

Preferably, the air outlet end of the base housing of the device of the present invention is a monotube, whereas the air inlet end of the base housing comprises two or more branched tubes such that said two or more porous filtration materials are disposed therein.

Preferably, each of said air outlet end and air inlet end of the base housing of the device of the present invention is a monotube, and the two or more porous filtration materials of the pre-filter are constructed as concentric rings surrounding a center disk.

Preferably, the pre-filter is composed of two porous filtration materials.

Preferably, the porous filtration materials of the device of the present invention are made of a foam material, a sintered glass material, or a porous ceramic material.

DETAILED DESCRIPTION OF THE INVENTION

Figure 1:
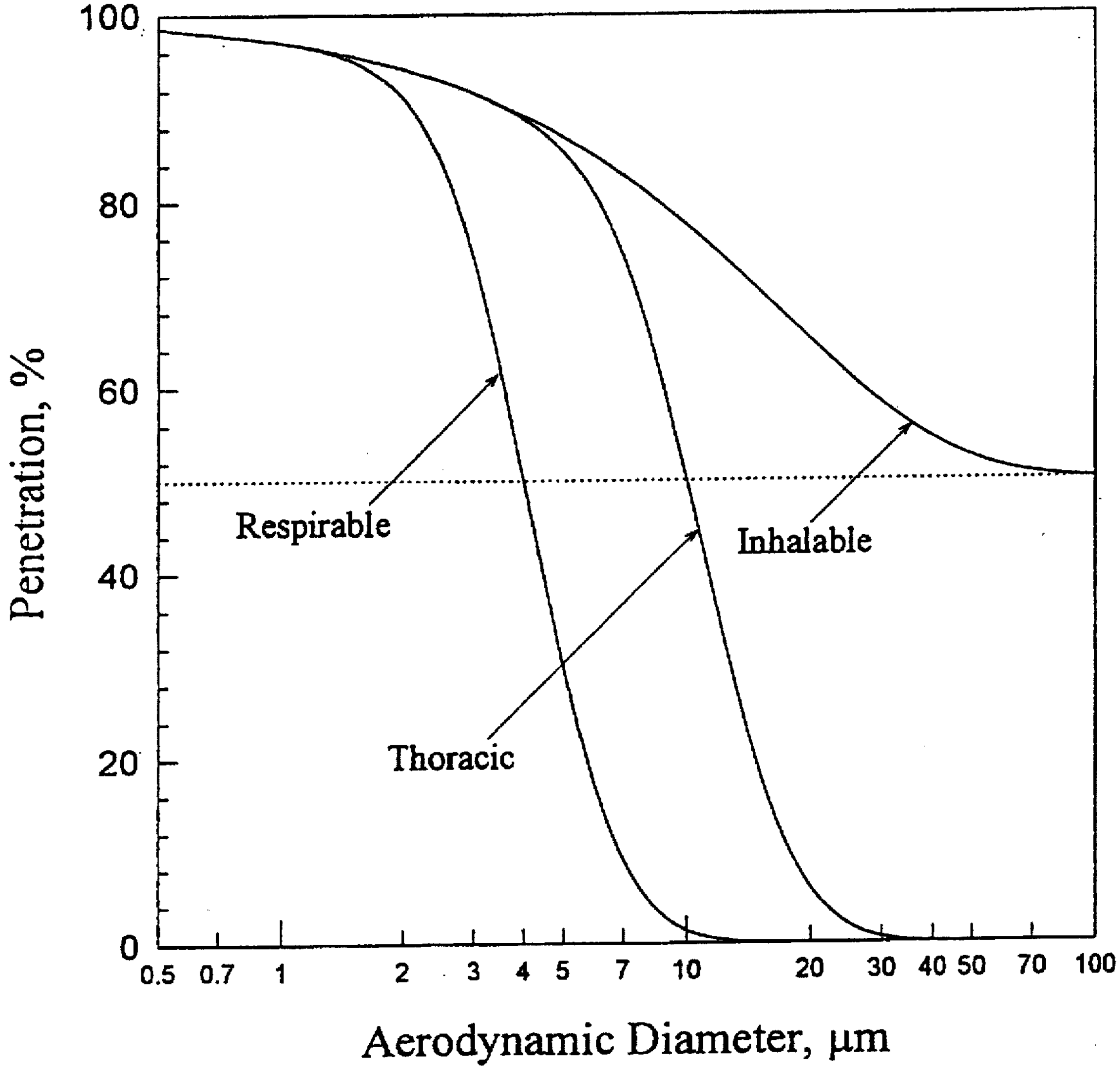
FIG. 1 shows three internationally-defined aerosol size-selective sampling curves.
Figure 2:
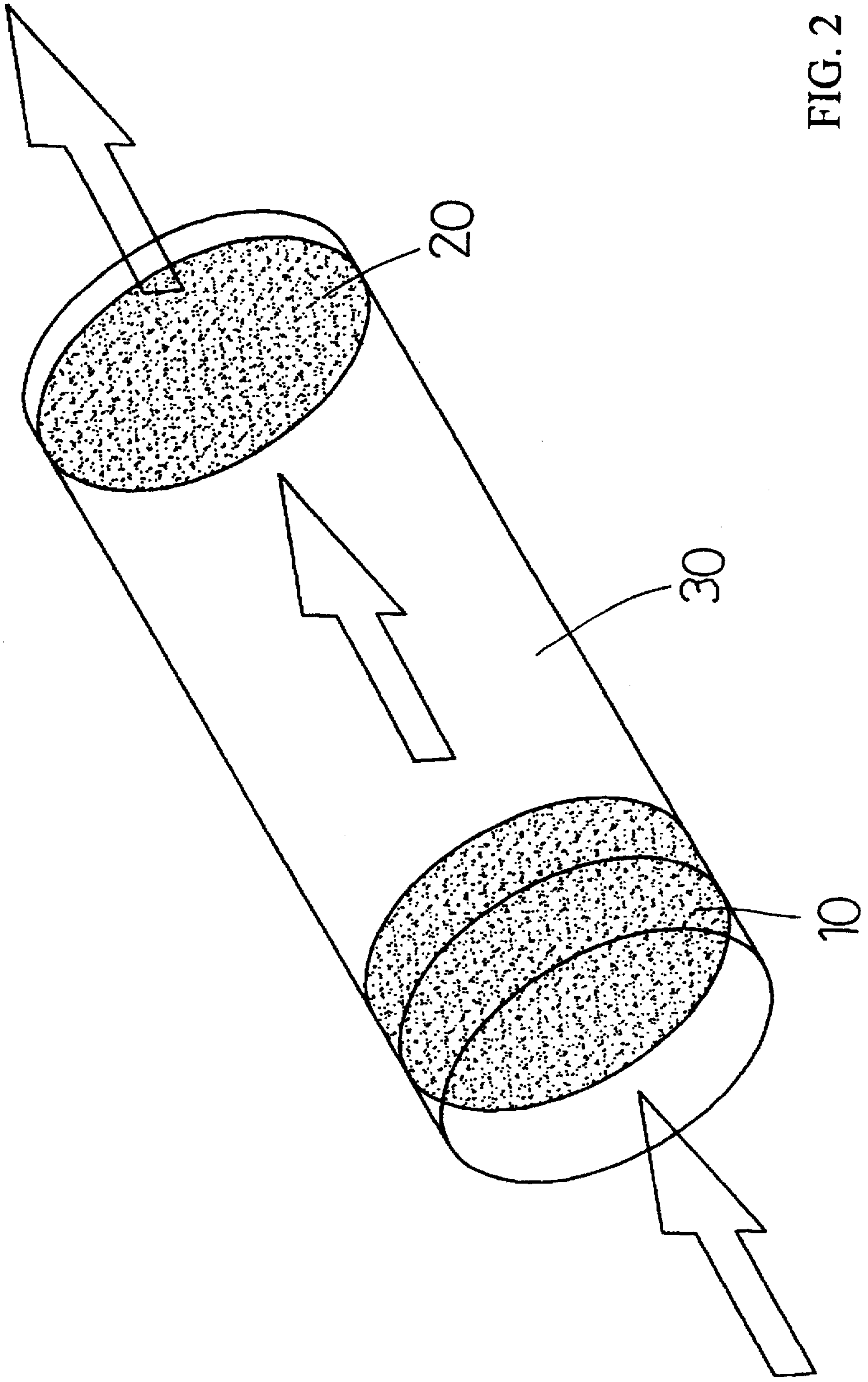
FIG. 2 shows a schematic view of an aerosol size-selective sampling device of the prior art.

For comparison, a prior art aerosol size-selective sampling device is first described. As shown in FIG. 2, an aerosol size-selective sampling device of the prior art comprises a pre-filter 10, a collector 20, and a base housing 30. The air pumping direction is indicated by an arrow. The filter paper is used as the collector 20, whereas a foam body made of polyurethane, polyester or polyether is used as the pre-filter 10.

Figure 3:
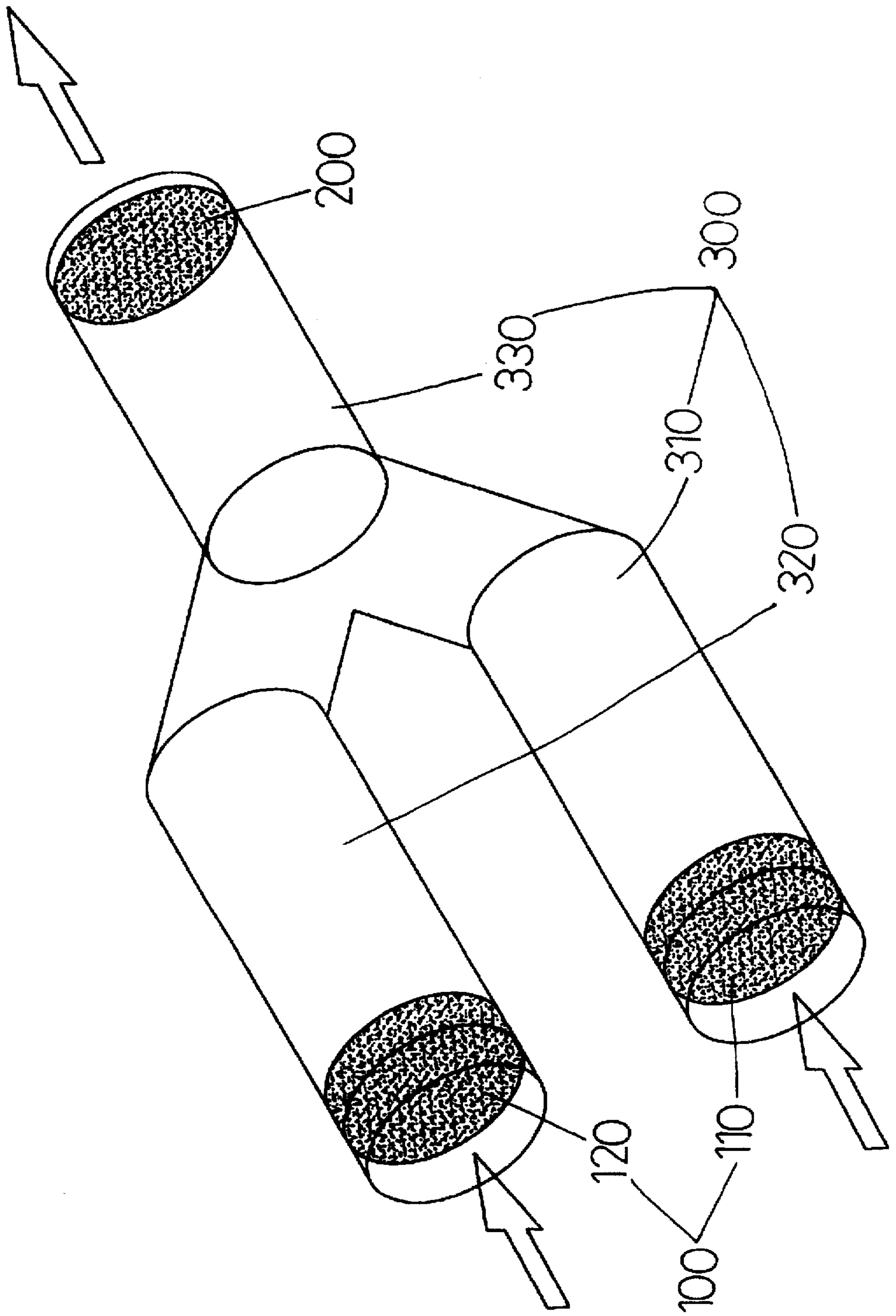
FIG. 3 shows a schematic view of a first preferred embodiment of the present invention.

As shown in FIG. 3, an aerosol size-selective sampling device of the first preferred embodiment of the present invention is composed of a pre-filter 100, a collector 200, and a Y-shaped base housing 300. The pre-filter 100 is made up of a foam body 110 of a low porosity and a foam body 120 of a high porosity. The base housing 300 comprises a first parallel tube 310, a second parallel tube 320, and a single tube 330 connecting the first parallel tube 310 and the second parallel tube 320. The foam bodies 110 and 120 are located respectively in the inlet ends of the first parallel tube 310 and the second parallel tube 320. The collector 200 is located in one end of the single tube 330. The air pumping direction is indicated by an arrow. The collector 200 is in fact the filter paper. The pre-filter 100 is a foam body made of polyurethane (PU), polyester, or polyether. The pre-filter 100 may be also made of a sintered glass or porous ceramic material.

Figure 4:
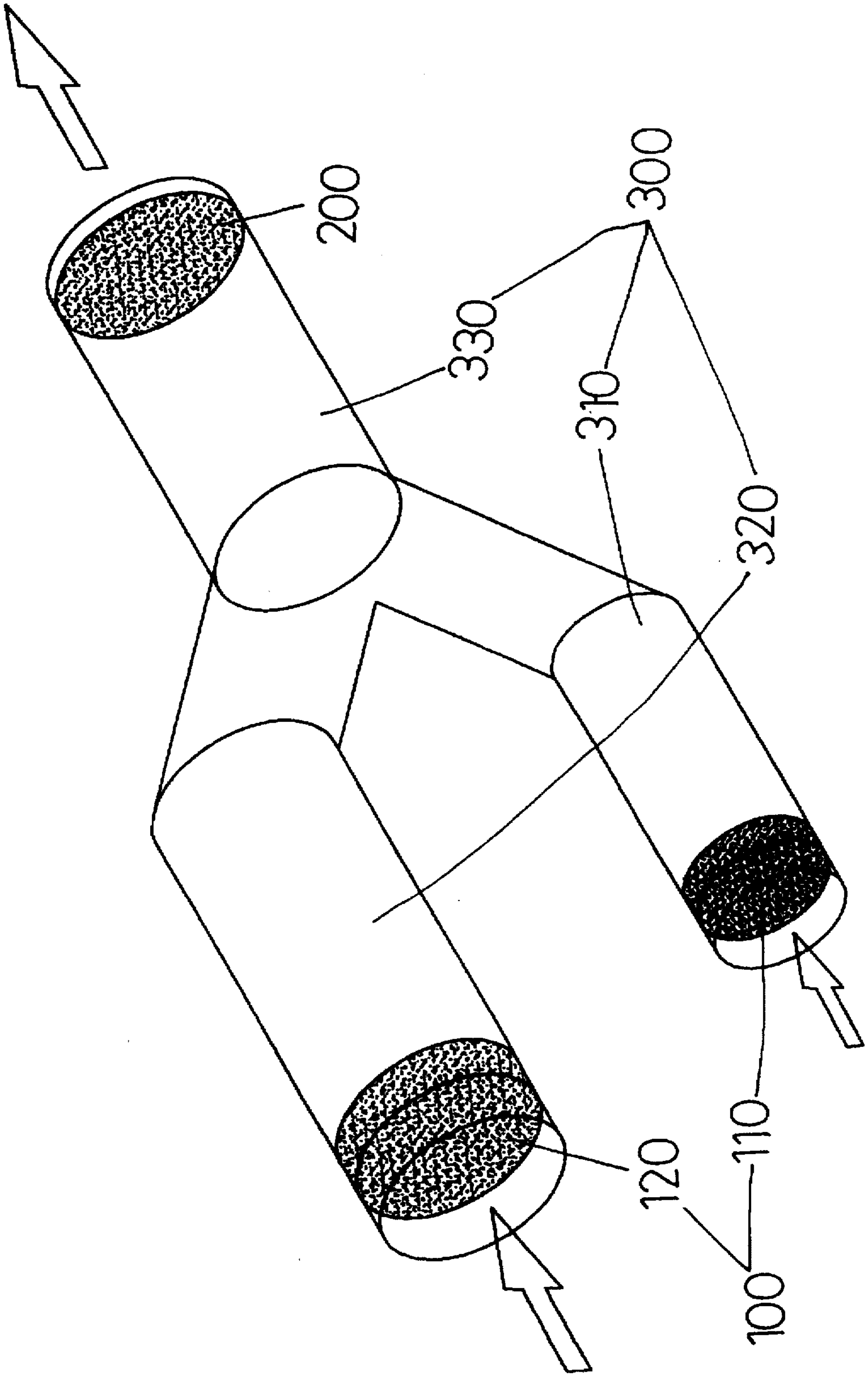
FIG. 4 shows a schematic view of a second preferred embodiment of the present invention.

Now referring to FIG. 4, an aerosol size-selective sampling device of the second preferred embodiment of the present invention is similar in construction to that of the first preferred embodiment of the present invention, with the difference being that the first parallel tube 310 and the second parallel tube 320 are different in diameter, and that the foam body 110 and the foam body 120 are different in diameter.

Figure 5:
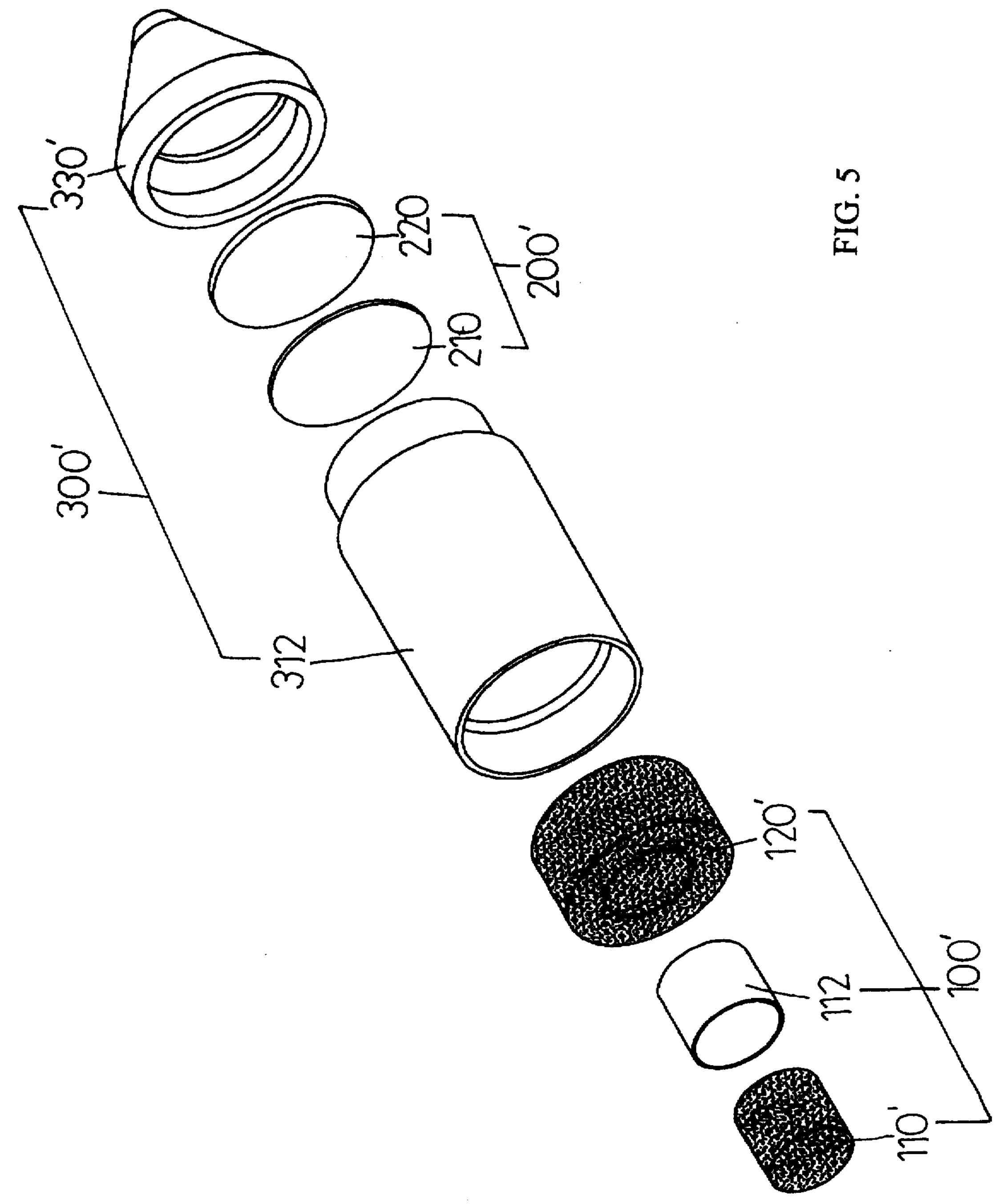
FIG. 5 shows a schematic view of a third preferred embodiment of the present invention.
Figure 6:
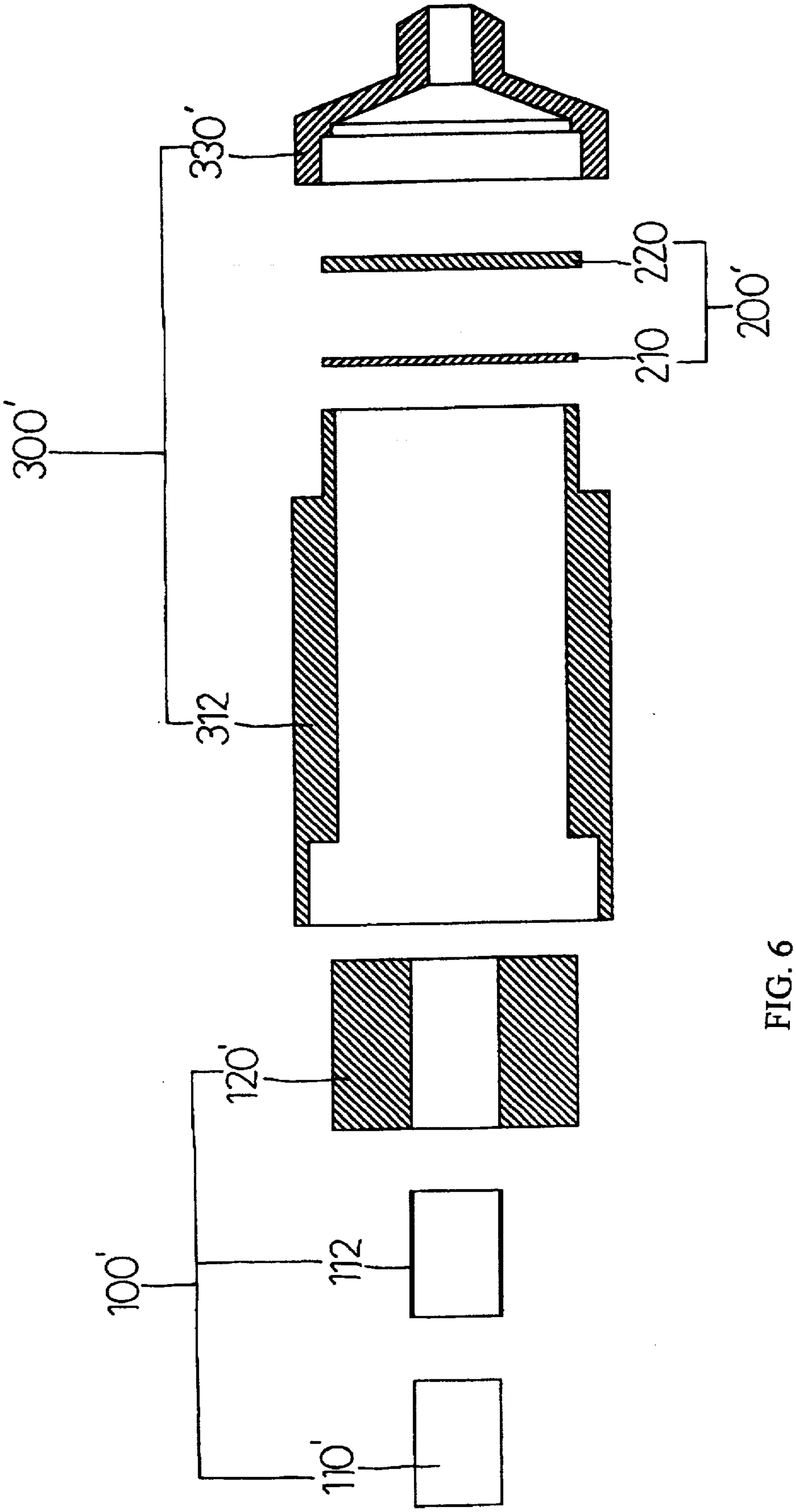
FIG. 6 shows a sectional view of the third preferred embodiment of the present invention.

As illustrated in FIGS. 5 and 6, an aerosol size-selective sampling device of the third preferred embodiment of the present invention is composed of a pre-filter 100', a collector 200', and a cylindrical base housing 300'.

The pre-filter 100' is composed of a cylindrical foam body 110' of a low porosity, a ring-shaped foam body 120' of a high porosity, and a separation tube 112. The cylindrical foam body 110' is first fitted into the separation tube 112 and is then fitted into the center of the ring-shaped foam body 120' such that the cylindrical foam body 110' is concentric with the ring-shaped foam body 120'. The collector 200' is composed of a filter paper 210 which is supported by a backing board 220. The base housing 300' comprises a pre-filter fastening tube 312 and a collector fastening tube 330'. The pre-filter 100' is fastened with the fastening tube 312 such that the pre-filter 100' is located at an air inlet. The pre-filter fastening board 220 and the filter paper 210 are located at the right end of the collector fastening tube 330' before being fitted into the left end of the pre-filter fastening tube 312.

The aerosol size-selective sampling device of the present invention is basically similar in construction to that of the prior art, with the difference being that the pre-filter of the device of the present invention is composed of two or more porous filtration materials arranged in a parallel manner such that the colloidal particles of aerosol are guided in a parallel and diverting manner to deposit in the sampling device.

The porous filtration material used in the device of the present invention is similar in porosity to the device of the prior art. The preferred porosity ranges between 5 and 200 ppi (pore per inch). However, it is suggested that the porosity in the range of 10–100 ppi is most preferred. The parallel filtration materials are preferably different in porosity, with the difference ranging between 2 and 50 times, or more preferably between 5 and 20 times.

The pre-filter of the device of the present invention is preferably comprises two porous filtration materials which are provided with a surface area facing the flow direction of the air. The surface area ratio of the filtration material of a high porosity and the filtration material of a low porosity is preferably in the range of 10:1 to 1:10, and more preferably in the range of 8:1 to 1:5, and still more preferably in the range of 6:1 to 1:2.

The operational conditions of the aerosol size-selective sampling device of the present invention are similar to those of the device of the prior art.

The features of the present invention will be more readily understood upon a thoughtful deliberation of the following detailed description of the embodiments of the present invention in conjunction with the accompanying drawings as well as the comparative study of various relevant examples.

In view of the technical difficulties that are involved in the production and the control of the aerosol having larger particle diameters, the internationally-defined inhalable deposition curves have not been established indisputably and are therefore subject to a great deal of debate. In addition, the current research data on the aerosol having an aerodynamic diameter greater than 100 μm are rather insufficient. Moreover, the sampling devices, such as the thoracic sampling device, are not available. The thoracic sampling device developed by the United States EPA is not widely adopted at best. As a result, the emphasis of the present invention is placed on the respirable aerosol.

In both the comparative example and the embodiments of the present invention, a peristaltic pump and an ultrasonic atomizing nozzle were used to establish the system for producing the respirable aerosols. The peristaltic pump (Model 7550-90) was made by Cole-Parmer Instrument Co., Niles, Ill., U.S.A., whereas the ultrasonic atomizing nozzle (Model 3050) is a product of Sono-Tek Inc., Ponghkeepsie, N.Y., U.S.A. The liquid was transported by means of two peristaltic pumps, which were controlled by a computer system, thereby enabling the linear change in the flow of the liquid to take place in a predetermined period of time. The flow of the transported liquid ranged between 0.01 and 0.6 ml/min. The two peristaltic pumps had a rotating speed ranging between 1 and 60 RPM. The application of the ultrasonic atomizing nozzle is based on the principle that the electrical energy is converted into the mechanical energy by a piezoelectric transducer, thereby generating the high frequency ultrasonic wave capable of crashing the liquid into the droplets in the nozzle. The particle diameter distribution is dependent on the nozzle frequency, the surface tension of the liquid, and the liquid density, which the nozzle frequency being the most important factor determining the particle diameter of the droplets. According to the frequency set up by the manufacturer, the ultrasonic atomizing nozzle is capable of producing the droplets having a diameter ranging between 30 and 70 µm. A desired aerosol having a desired range of diameters are generated by using the peristaltic pumps in conjunction with the control of the liquid composition.

The particle diameter distribution range of the aerosol must cover the respirable size-selective sampling. It is therefore necessary to produce the aerosol having the count median diameter (CMD) ranging between 1 and 10 µm. DOP (dioctyl phthalate) is used as a material for making the aerosol.

It was necessary to employ a testing chamber in the experiment. The air, which was filtered by a high-efficient filtration material, was injected into the chamber at the rate of 90 L/min. for drying and mixing the aerosol. The space inside the testing chamber was about $0.35*0.35*2.2\ m^3$. Located at the bottom was an exhaust duct for removing the exhaust gas produced in the experiment. The aerosol, which were freshly formed by the peristaltic pumps in the testing chamber, were generally carry electrical charges. As a result, the testing chamber was provided therein with a neutralizer to minimize the impact of the electrical charges of the aerosol on the experiment. The neutralizer was made by Static Control Services, Palm Springs, Calif., U.S.A. The neutralizer was capable of ionizing the air by means of high voltage so as to produce the bipolar ions of high concentration for neutralizing the electrical charges of the aerosol. As a result, the Boltzman Equilibrium was attained in a short period of time.

The testing chamber of the experiment was also provided with an aerosol electrometer (Model 3068, TSI Inc., St. Paul, Minn., U.S.A.) for making sure that the electrical equilibrium was attained. The aerosol electrometer is composed of a filter paper located in the Faraday's cup, and an electric current meter. The filter paper was capable of collecting the electrical charges of the aerosol along with the aerosol, thereby causing the Faraday's cup to be charged electrically. The current value of the Faraday's cup was measured by the electric current meter, so as to make sure that the electrical charge equilibrium of the system was attained.

The aerosol concentration and the particle diameter were measured by an Aerosizer (Model 8000, Amherst Process Instrument Inc., Hadley, Mass., U.S.A.), which was capable of measuring the particle diameter ranging between 0.01 µm and 200 µm. The sampling flow rate was 6 L/min. The application of the Aerosizer is based on the principle that the aerosol are forced through two laser beams via an acceleration flow field, and that the time of flight (TOF) between the two laser beams is measured so as to calculate the particle diameters of the aerosol.

The sampling efficiency, especially the aspiration efficiency, of the aerosol having a particle diameter greater than 1 µm is often affected by such factors as the aerosol particle diameter, the ratio of wind velocity inside and outside the sampling tube, and the sampling angle. In the penetration experiments of the following comparative examples 1–11 and the embodiment 6, the Aerosizer was connected with the Y-shaped tube, which was provided in one branch tube thereof with a sampling device. By switching the opening of the branch tubes, the background aerosol and the aerosol passing through the sampling device could be made to pass through substantially the same sampling route so as to avert the adverse impact on the sampling efficiency. In the embodiments 1–5, the foam body of the sampling device was directly loaded and unloaded to carry out the penetration experiments. By using the Aerosizer, the concentrations of different-diameter particles of the aerosol, which passed through or bypassed the sampling device, were measured. The penetration rates of various aerodynamic diameters were calculated based on the measured values of the concentrations of different-diameter particles.

In the following comparative examples and the embodiments, polyurethane foams having the density of 0.810 and the packing density of 0.0264 were used as the porous filtration materials. On the basis of the examination done with the electron microscope, the porosity was calculated to be in the range of 10–100 pores per inch (ppi). In the meantime, the sampling device was not provided therein with the collector (filter paper) in the penetration experiment.

COMPARATIVE EXAMPLES 1–3 (CHANGING POROSITY OF THE POROUS FILTRATION MATERIAL)

By using the conventional aerosol size-selective sampling device as shown in FIG. 2, the penetration experiment on the DOP aerosol was carried out. The DOP aerosol had a weight concentration of 180 $mg/m^3$ and a diameter distribution wherein particles having a particle diameter of 10 µm are the maximum. The porous filtration materials had a diameter of 25 mm and a thickness (X) of 10 mm. The surface flow velocity (U) was 27.2 cm/s. The porosity (N) is shown in the following table. The experimental results are shown in the following table as well as FIG. 7.

| Comparative Examples | Porosity (N), (ppi) | 50% Cut-off Size ($D_{50}$), µm | Slope, Absolute Value (S) |
|---|---|---|---|
| 1 | 100 | 4.220 | 0.360 |
| 2 | 70 | 6.098 | 0.249 |
| 3 | 40 | 7.214 | 0.177 |

Figure 7:
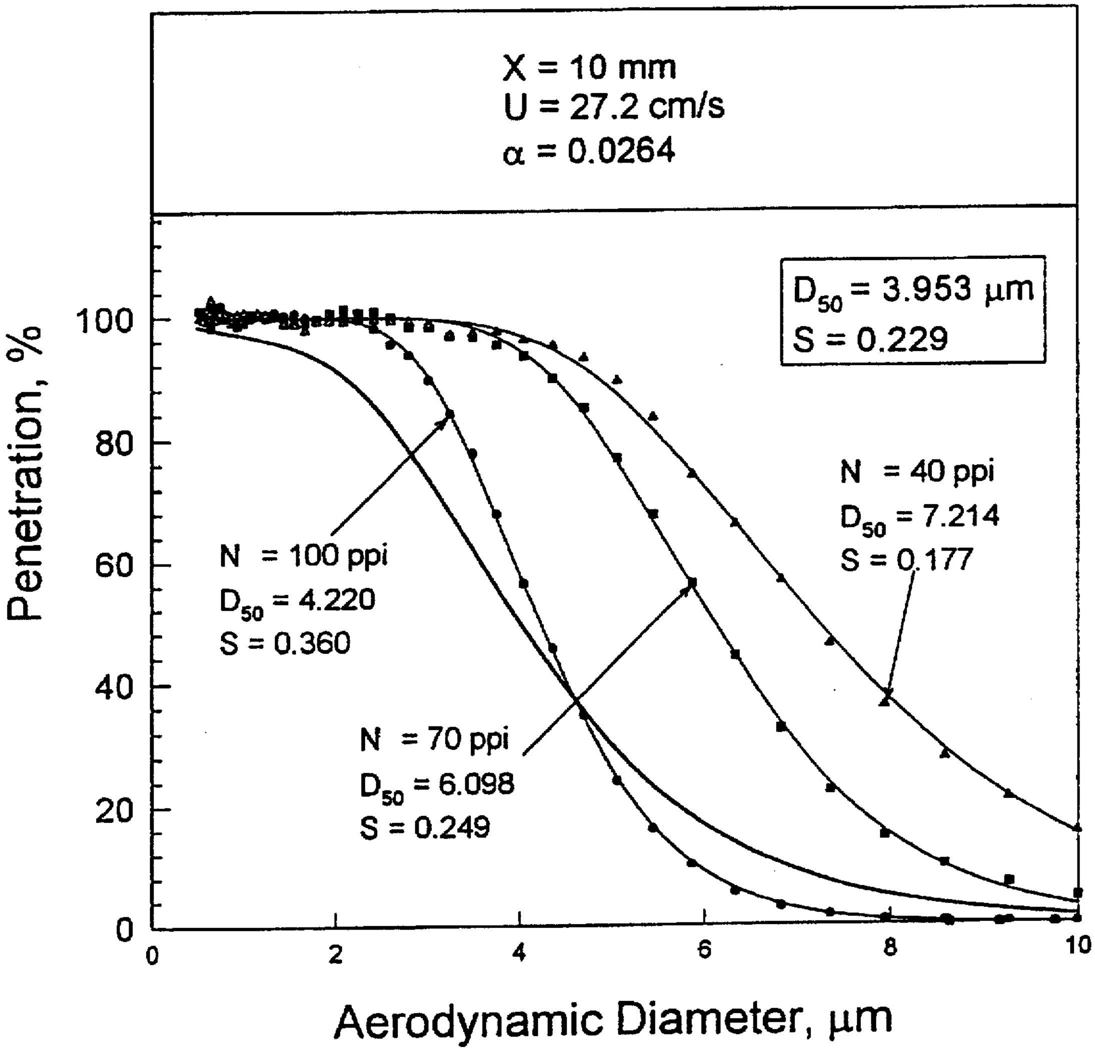
FIG. 7 shows the best-fitting curves of the aerosol penetration rates obtained by the aerosol size-selective sampling device of the prior art, with the solid bold curves representing the internationally-defined respirable curves, and with different symbols representing the penetration rates obtained by the foam bodies having different porosities.

As shown in FIG. 7, there is a great deviation between the aerodynamic diameter-penetration rate best-fitting curves of the comparative examples 1–3 and the internationally-defined respirable aerosol curves which are designated by the solid curves without the indicating symbols. In addition, their cut-off sizes ($D_{50}$) and absolute values of slope (S) are not in conformity with the standard values of $D_{50}$=3.953 and S=0.229.

COMPARATIVE EXAMPLES 4–6 (CHANGING THE THICKNESS OF THE POROUS FILTRATION MATERIAL)

Figure 8:
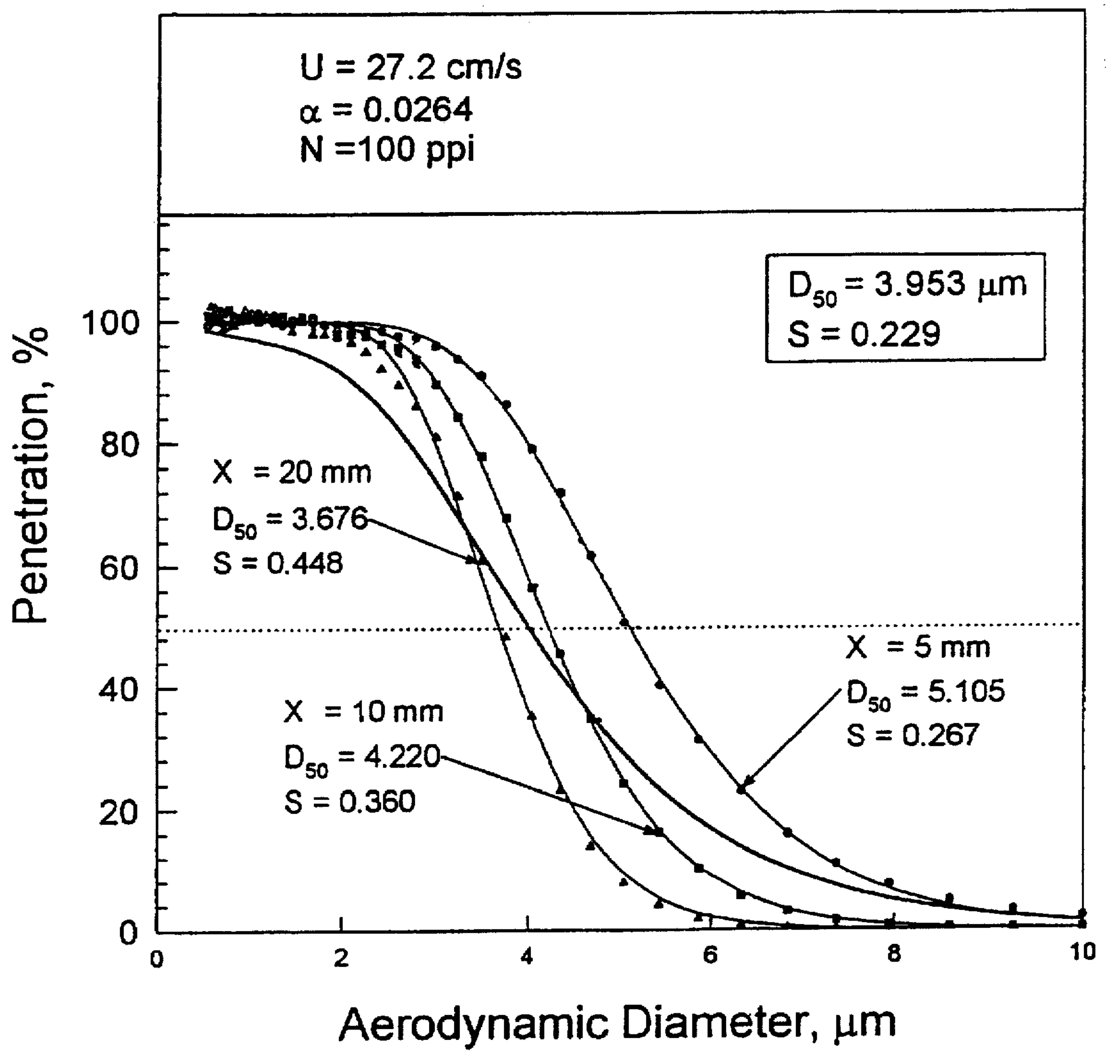
FIG. 8 shows the best-fitting curves of the aerosol penetration rates obtained by the aerosol size-selective sampling device of the prior art, with the solid bold curves representing the internationally-defined respirable curves, and with different symbols representing the penetration rates obtained by the foam bodies different in thickness.

The porosity (N) of the porous filtration materials was fixed at 100 ppi, whereas the thickness (X) of the porous filtration materials was changed. The procedure of the Comparative Example 1 was repeated. The experimental results are shown in FIG. 8 as well as the following table.

| Comparative Examples | Thickness (X), (mm) | 50% Cut-off Size ($D_{50}$), µm | Slope, Absolute Value (S) |
|---|---|---|---|
| 4 | 20 | 3.676 | 0.448 |
| 5 | 10 | 4.220 | 0.360 |
| 6 | 5 | 5.105 | 0.267 |

COMPARATIVE EXAMPLES 7–10 (CHANGING SURFACE WIND VELOCITY)

The surface wind velocity (U) of the porous filtration materials was changed. The procedure of the Comparative Example 1 was repeated. The experimental results are shown in FIG. 9 and the following table.

| Comparative Examples | Wind Velocity (U), (cm/s) | 50% Cut-off Size ($D_{50}$), µm | Slope, Absolute Value (S) |
|---|---|---|---|
| 7 | 54.3 | 2.796 | 0.600 |
| 8 | 40.7 | 3.330 | 0.455 |
| 9 | 27.2 | 4.220 | 0.360 |
| 10 | 13.6 | 6.317 | 0.235 |

Figure 9:
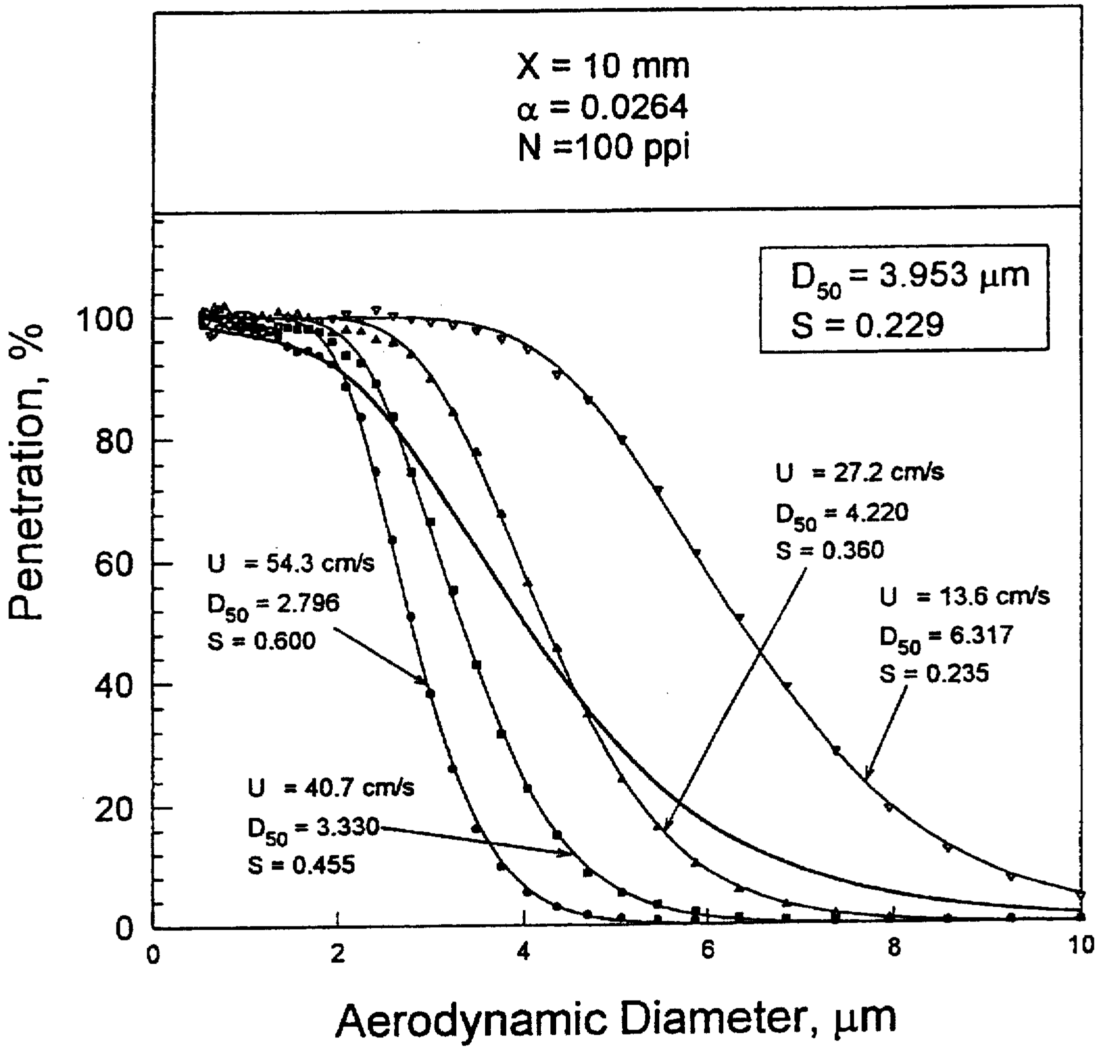
FIG. 9 shows the best-fitting curves of the aerosol penetration rates obtained by the aerosol size-selective sampling device of the prior art, with the solid bold curves representing the internationally-defined respirable curves, and with different symbols representing the penetration rates obtained by the foam bodies having different surface wind velocities.

As shown in FIGS. 8 and 9, there is a great deviation between the aerodynamic diameter-penetration best-fitting curves of the comparative examples 4–10 and the internationally-defined respirable aerosol curves which are designated by the solid curves without being indicated by the symbols. In addition, their $D_{50}$ and S values are not in conformity with the standard values of $D_{50}$=3.953 and S=0.229.

On the basis of the Comparative Examples 1–10, it can be concluded that the results of the comparative examples deviate greatly from the internationally-defined respirable aerosol sampling curves, and that the changes in the porosity, the thickness and the surface wind velocity of the porous filtration materials have failed to eliminate such deviation.

COMPARATIVE EXAMPLE 11 (SERIAL SIZE-SELECTIVE SAMPLING)

Figure 10:
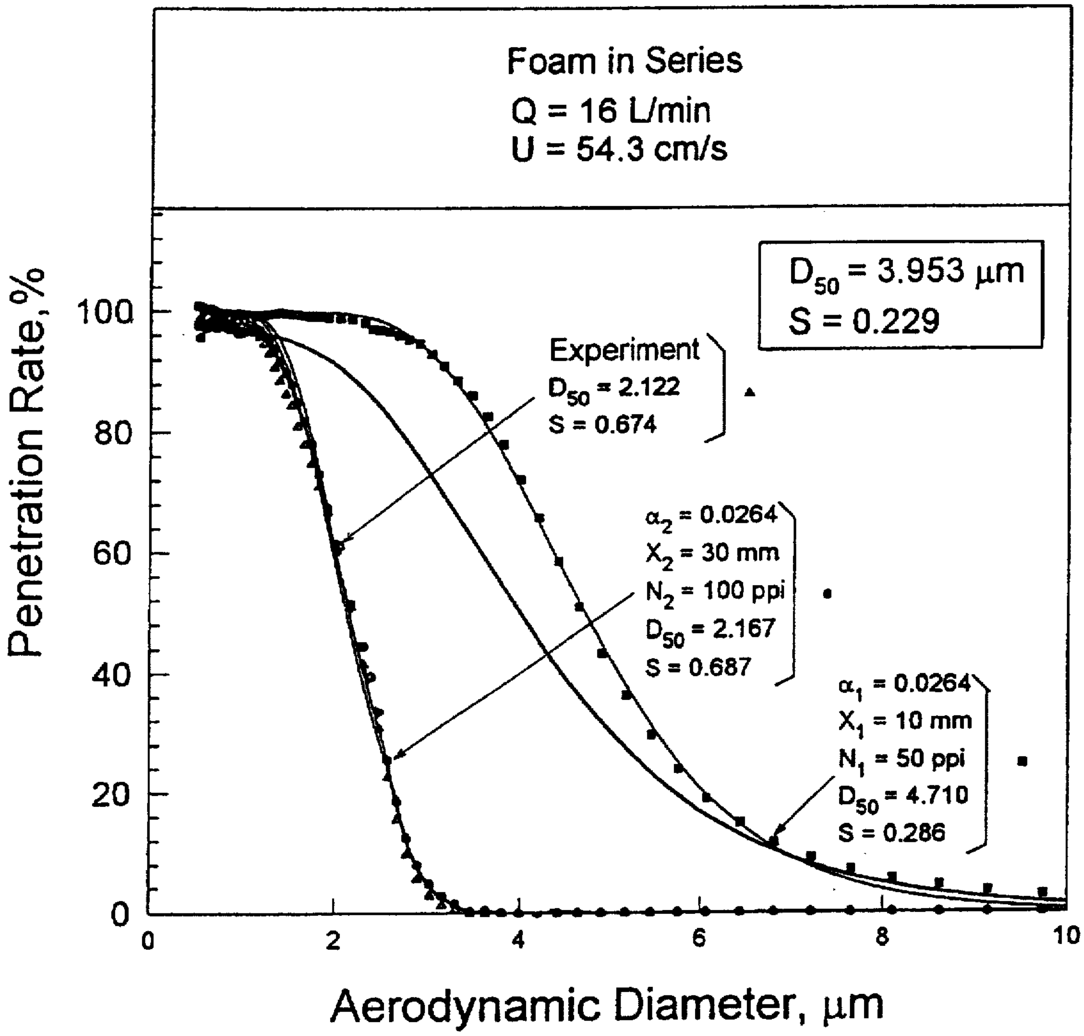
FIG. 10 shows the best-fitting curves of the aerosol penetration rates obtained by the aerosol size-selective sampling device of the prior art, with the solid bold curves representing the internationally-defined respirable curves, and with different symbols representing the penetration rates obtained by the device comprising two foam bodies different in porosity and arranged in a serial fashion, and the devices comprising individual foam body.

The DOP aerosol penetration experiment was conducted by using a sampling device which was composed of two porous filtration materials different in porosity. The two porous filtration materials were arranged in series. The DOP aerosol had a weight concentration of 180 mg/m$^3$ and a diameter distribution wherein particles having a particle diameter of 10 µm are the maximum. The surface flow speed (U) was 54.3 cm/s. Two porous filtration materials had a diameter of 25 mm. The first filtration material had a thickness ($X_1$) of 10 mm and a porosity ($N_1$) of 50 ppi, whereas the second filtration material had a thickness ($X_2$) of 30 mm, and a porosity ($N_2$) of 100 ppi. The results are shown in FIG. 10 and the following table. The data of the first filtration material alone and the data of the second filtration material alone are also included.

| Comparative Example | $N_1$ (ppi) | $N_2$ (ppi) | $X_1$ (mm) | $X_2$ (mm) | $D_{50}$ (µm) | S |
|---|---|---|---|---|---|---|
| — | 50 | — | 10 | — | 4.710 | 0.286 |
| — | — | 100 | — | 30 | 2.167 | 0.687 |
| 11 | 50 | 100 | 10 | 30 | 2.122 | 0.674 |

As shown in FIG. 10, there is a great deal of deviation between the aerodynamic diameter-penetration best-fitting curves of the comparative example 11 and the internationally-defined respirable aerosol curves which are designated by the solid curves without being identified by the symbols. In addition, their $D_{50}$ and S values are not in conformity with the standard value of $D_{50}$=3.953 and the standard value of S=0.229.

EMBODIMENT 1

Figure 11:
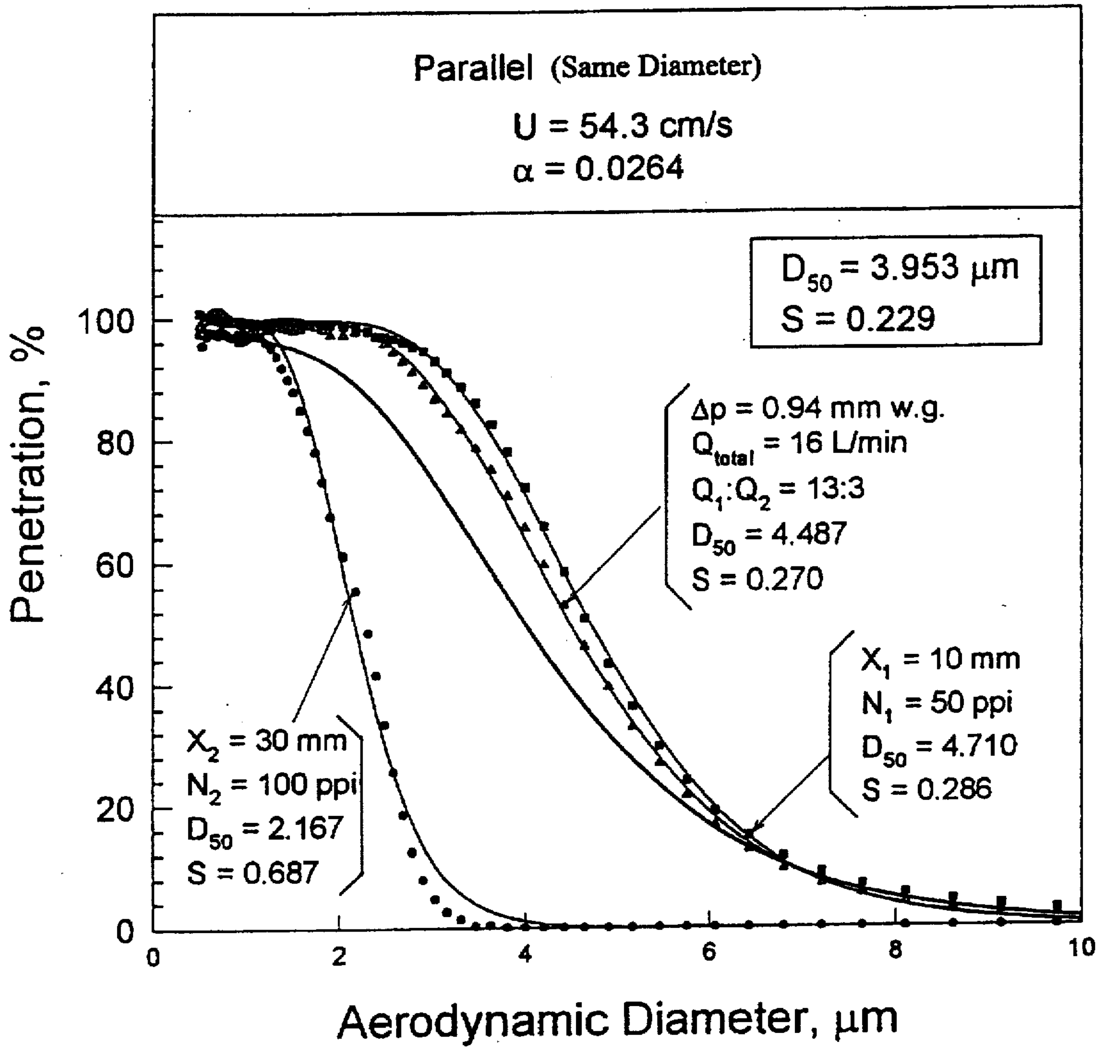
FIG. 11 shows the best-fitting curves of the aerosol penetration rates obtained respectively by the aerosol size-selective sampling devices of the present invention and the prior art, with the solid bold curves representing the internationally-defined respirable curves, and with different symbols representing the penetration rates obtained by the device comprising two foam bodies different in porosity and arranged in a parallel manner, and the devices comprising individual foam body.

The penetration experiment was conducted by using the device composed of the parallel tubes having a diameter (d) of 25 mm, as shown in FIG. 3. The DOP aerosol had a weight concentration of 180 mg/m$^3$ and a diameter distribution wherein particles having a particle diameter of 10 µm are the maximum. The surface flow speed (U) of 54.3 cm/s. The porosities and the thickness of the two parallel filtration materials are $N_1$=50 ppi, $N_2$=100 ppi, $X_1$=10 mm, $X_2$=30 mm. The results obtained by using only one filtration material are also shown in FIG. 11 and the following table. In FIG. 11, the sum of flow rate is designated by $Q_{total}$, whereas $Q_1$ and $Q_2$ stand respectively for the flow rates of the two parallel tubes. The filtration material, which has greater porosity and thickness, is shown to have a smaller flow.

| Embodiment | $N_1$ (ppi) | $N_2$ (ppi) | $X_1$ (mm) | $X_2$ (mm) | $D_{50}$ (µm) | S |
|---|---|---|---|---|---|---|
| — | 50 | — | 10 | — | 4.710 | 0.286 |
| — | — | 100 | — | 30 | 2.167 | 0.687 |
| 1 | 50 | 100 | 10 | 30 | 4.487 | 0.270 |

On the basis of FIGS. 10 and 11, it is readily apparent that the result of the parallel filtration materials is more in line with the internationally-defined respirable aerosol sampling curve, and that the result of the serial filtration materials is less in line with the internationally-defined respirable aerosol sampling curve.

EMBODIMENT 2

Figure 12:
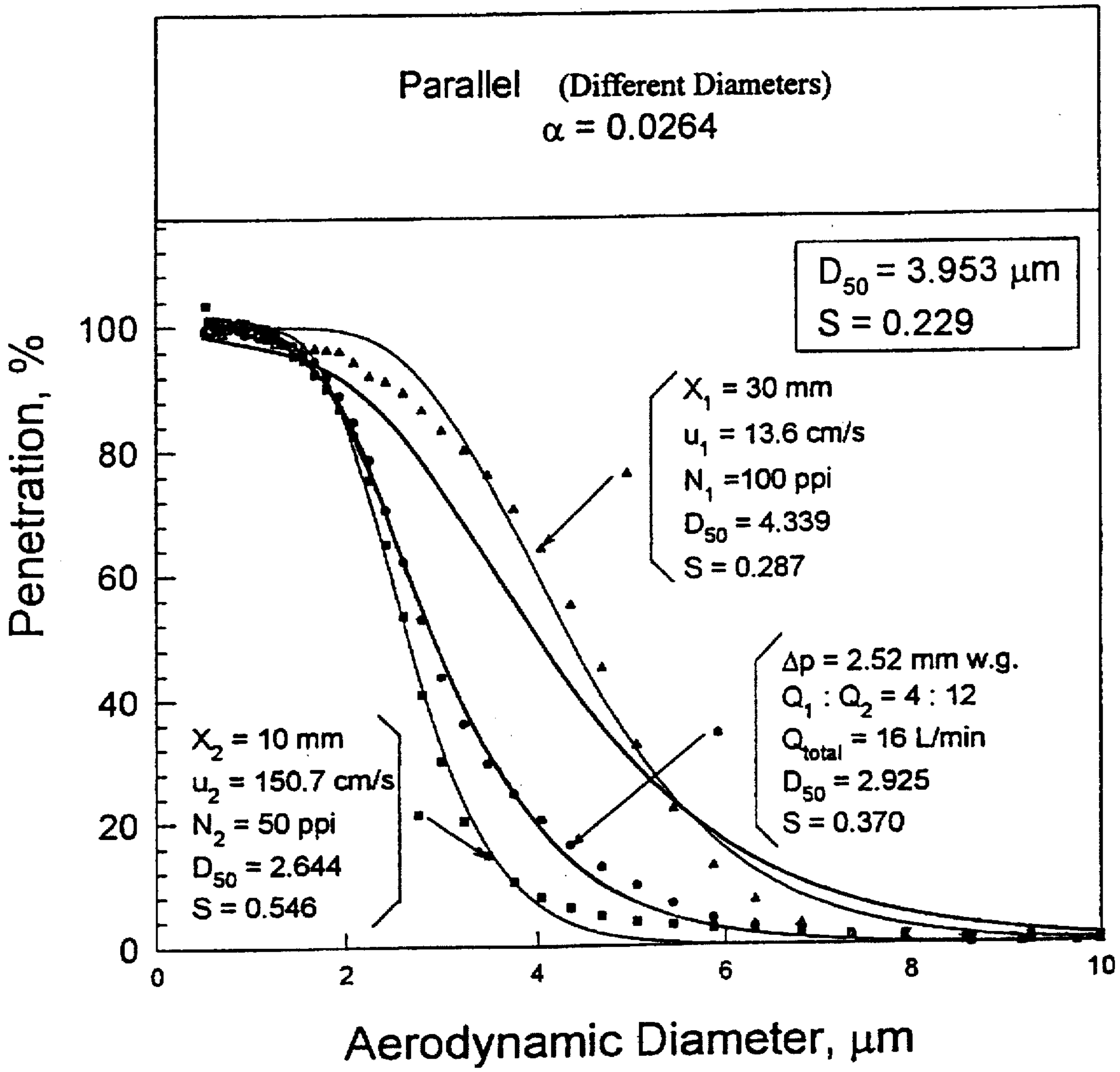
FIG. 12 shows the best-fitting curves of the aerosol penetration rates obtained respectively by the aerosol size-selective sampling devices of the present invention and the prior art, with the solid bold curves representing the internationally-defined respirable curves, and with different symbols representing the penetration rates obtained by the device comprising two foam bodies different in porosity and diameter and arranged in a parallel manner, and the devices comprising individual foam body.

The penetration experiment was conducted by using the device composed of the parallel tubes having different diameters ($d_1$=25 mm; $d_2$=13 mm), as shown in FIG. 4. The DOP aerosol had a weight concentration of 180 mg/m$^3$ and a diameter distribution wherein particles having a particle diameter of 10 µm are the maximum. The porosity and the thickness of the two parallel filtration materials are $N_1$=100 ppi, $N_2$=50 ppi, $X_1$=30 mm ($d_1$=25 mm), $X_2$=10 mm ($d_2$=13 mm), whereas the surface wind velocity of the two parallel filtration materials disposed in the parallel tubes are respectively $U_1$=13.6 cm/s, and $U_2$=150.7 cm/s. The results obtained by using only one filtration material are also shown in FIG. 12 and the following table. In FIG. 12, the sum of flow rate is designated as $Q_{total}$ while the flows of the two parallel tubes are designated respectively by $Q_1$ and $Q_2$.

| Embodiment | $N_1$ (ppi) | $N_2$ (ppi) | $X_1$ (mm) | $X_2$ (mm) | $D_{50}$ (μm) | S |
|---|---|---|---|---|---|---|
| — | 100 | — | 30 | — | 4.339 | 0.287 |
| — | — | 50 | — | 10 | 2.644 | 0.546 |
| 2 | 100 | 50 | 30 | 10 | 4.339 | 0.287 |

By comparing FIGS. 11–12, it is readily apparent that an appropriate change in the surface wind velocity of the filtration materials can result in a better conformity of the result with the internationally-defined respirable aerosol sampling curve.

EMBODIMENTS 3-5

Figure 13:
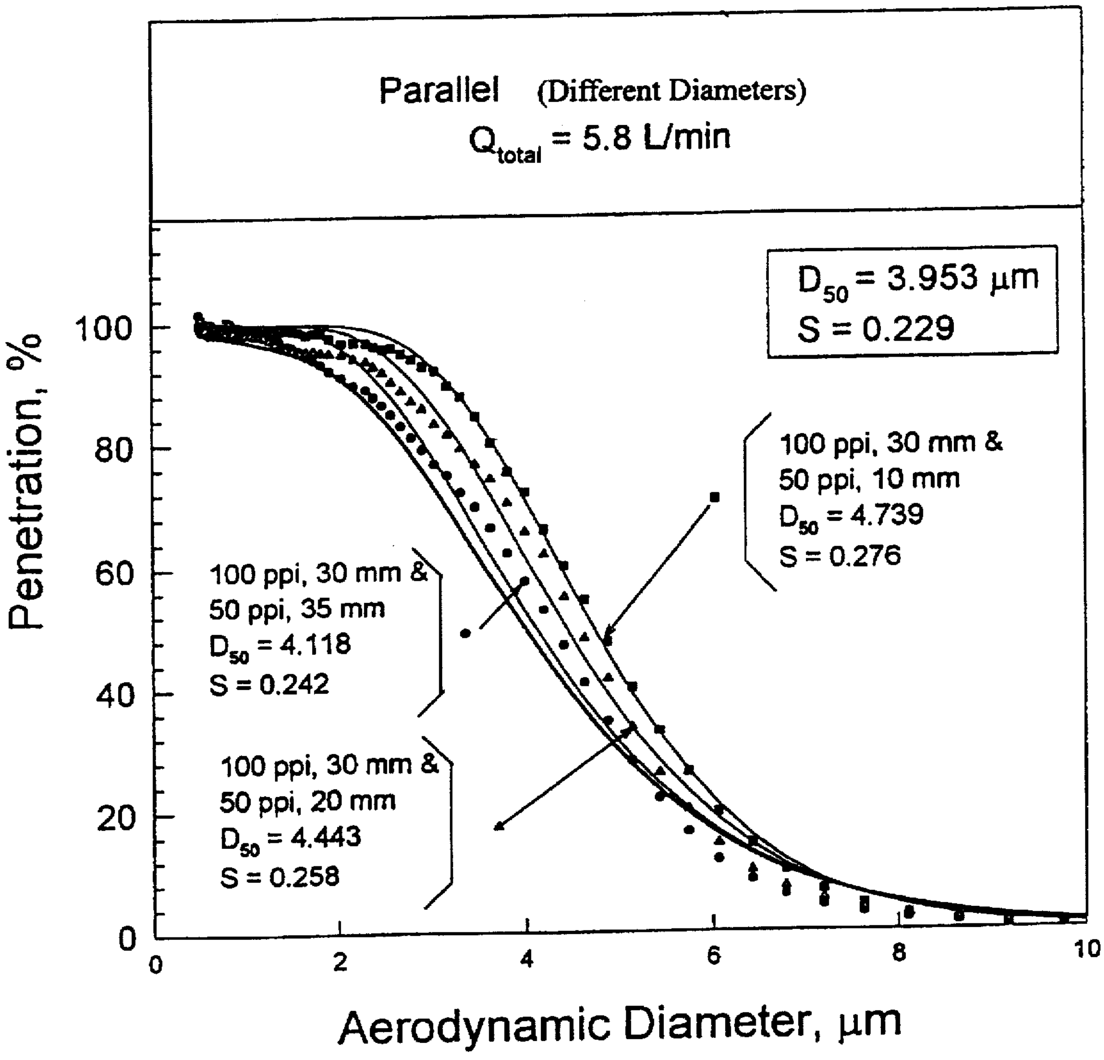
FIG. 13 shows the best-fitting curves of the aerosol penetration rates obtained by the aerosol size-selective sampling device of the present invention, with the solid bold curves representing the internationally-defined respirable curves, and with different symbols representing the penetration rates obtained by the devices comprising the foam bodies different in porosity and diameter, and arranged in a parallel manner.

The thickness ($X_2$) of the filtration material having the diameter ($d_2$=13 mm) was charged to 10, 20 and 35 mm. The procedure of the Embodiment 2 was repeated. In addition, the sum of flow rate ($Q_{total}$) was changed to 5.8 L/min. The experimental results are shown in FIG. 13 and the following table.

| Embodiment | $N_1$ (ppi) | $X_1$ (mm) | $N_2$ (ppi) | $X_2$ (mm) | $D_{50}$ (μm) | S |
|---|---|---|---|---|---|---|
| 3 | 100 | 30 | 50 | 35 | 4.118 | 0.242 |
| 4 | 100 | 30 | 50 | 20 | 4.443 | 0.258 |
| 5 | 100 | 30 | 50 | 10 | 4.739 | 0.276 |

EMBODIMENT 6

The penetration experiment was conducted by using the device shown in FIGS. 5 and 6. The DOP aerosol had a weight concentration of 180 mg/m$^3$ and a diameter distribution wherein particles having a particle diameter of 10 μm are the maximum. The sum of flow rate ($Q_{total}$) is 4.7 L/min. The cylindrical foam body 110' has a length of 35 mm, an outer diameter of 11.7 mm and a porosity of 50 ppi; and the ring-shaped foam body 120' has a length of 30 mm, an inner diameter of 11.6 mm, an outer diameter of 25.0 mm, and a porosity of 100 ppi. The results of this embodiment and the Embodiment 3 are shown together in FIG. 14 and the following table.

| Embodiment | $D_{50}$ | S |
|---|---|---|
| 3 | 4.118 | 0.242 |
| 6 | 4.270 | 0.236 |

Figure 14:
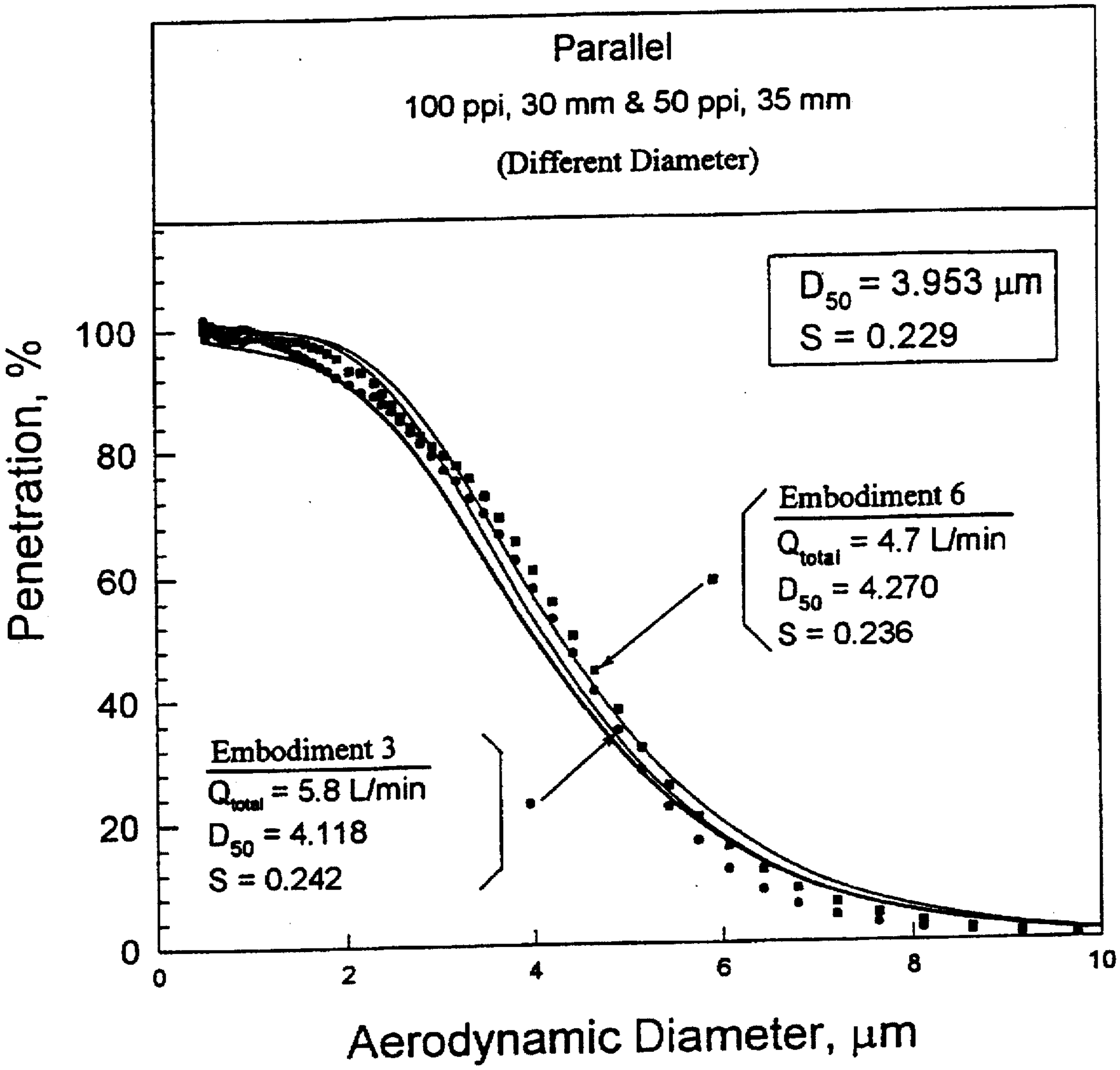
FIG. 14 shows the best-fitting curves of the aerosol penetration rates obtained by the aerosol size-selective sampling device of the present invention, with the solid bold curves representing the internationally-defined respirable curves, and with different symbols representing the penetration rates obtained by the devices comprising the foam bodies different in porosity and arranged in different parallel manners.

It is therefore readily apparent that the aerodynamic diameter-penetration rate best-fitting curves of the Embodiments 3 and 6 of the present invention are rather in line with the internationally-defined respirable aerosol sampling curves, which are indicated by the solid curves in FIG. 14.

What is claimed is:

1. An aerosol size-selective sampling method comprising taking an aerosol sample from a given atmospheric air by using an aerosol size-selective sampling device comprising a pre-filter, a base housing and a collector, wherein said pre-filter comprises two or more porous filtration materials disposed in an air inlet end of said base housing in a parallel manner, and said collector disposed in an air outlet end of said base housing, and wherein said atmospheric air is passed through said two or more porous filtration materials of said pre-filter in a parallel and diverting pattern before it is allowed to pass in a converging manner through said collector located in said air outlet end of said base housing, and said pre-filter is able to attain a desired penetration rate profile as a function of an aerodynamic diameter of aerosol contained in the atmospheric air within a predetermined range of said aerodynamic diameter.

2. The method as defined in claim 1, wherein said air inlet end of said base housing comprises two or more branched tubes for disposing said two or more porous filtration materials, and said air outlet end of said base housing is a monotube for disposing said collector therein.

3. The method as defined in claim 2, wherein said pre-filter is composed of two porous filtration materials.

4. The method as defined in claim 1, wherein said pre-filter is made up of a plurality of concentric rings surrounding a center disk, said air inlet end of said base housing is a monotube for disposing said pre-filter therein, and said air outlet end of said base housing is a monotube for disposing said collector therein.

5. The method as defined in claim 4, wherein said pre-filter is composed of two porous filtration materials.

6. The method as defined in claim 1, wherein said porous filtration materials are made of a foam material, a sintered glass material, or a porous ceramic material.

7. The method as defined in claim 6, wherein said porous filtration materials are made of a foam material.

8. An aerosol size-selective sampling device comprising:

a base housing provided at one end thereof with an air inlet end and at another end thereof with an air outlet end, said air outlet end adapted to accommodate a collector therein; and a pre-filter located in said air inlet end of said base housing, said pre-filter comprising two or more porous filtration materials arranged in a parallel manner.

9. The device as defined in claim 8, wherein said air inlet end of said base housing comprises two or more branched tubes for disposing said two or more porous filtration materials, and said air outlet end of said base housing is a monotube for disposing said collector therein.

10. The device as defined in claim 9, wherein said pre-filter is composed of two porous filtration materials.

11. The device as defined in claim 8, wherein said pre-filter is made up of a plurality of concentric rings surrounding a center disk, said air inlet end of said base housing is a monotube for disposing said pre-filter therein, and said air outlet end of said base housing is a monotube for disposing said collector therein.

12. The device as defined in claim 11, wherein said pre-filter is composed of two porous filtration materials.

13. The device as defined in claim 8, wherein said porous filtration materials are made of a foam material, a sintered glass material, or a porous ceramic material.

14. The device as defined in claim 13, wherein said porous filtration materials are made of a foam material.

* * * * *